United States Patent
Wang et al.

(10) Patent No.: US 7,144,714 B2
(45) Date of Patent: Dec. 5, 2006

(54) R2D2: AN ENZYME OF RNA SILENCING

(75) Inventors: Xiaodong Wang, Dallas, TX (US); Qinghua Liu, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 435 days.

(21) Appl. No.: 10/670,626

(22) Filed: Sep. 25, 2003

(65) Prior Publication Data

US 2005/0069990 A1 Mar. 31, 2005

(51) Int. Cl.
*C12P 19/34* (2006.01)
*C12P 21/06* (2006.01)
*C12Q 1/68* (2006.01)
*C07H 21/04* (2006.01)

(52) U.S. Cl. .................. 435/91.2; 435/6; 435/69.1; 536/24.5

(58) Field of Classification Search ............... None
See application file for complete search history.

(56) References Cited

OTHER PUBLICATIONS

Liu et al., 2003 Science 301:1921-1925.*
Tomari et al., 2004 Science 306:1377-1380.*
Meister et al., 2004, Nature 431:343-349.*
Pellino et al., 2003, Cell 115(2):132-133).*
Bernstein et al., 2001, Nature 409:363-6.*
Thornton et al., 2000, Nature Struct. Biol. 7 (Suppl.)991-994.*
Gerwitz et al. (1998) Blood 92(3):712-736.*
Greco et al. (2002) Frontiers in Bioscience 7:d1516-1524.*

* cited by examiner

*Primary Examiner*—Sean McGarry
*Assistant Examiner*—Louis V. Wollenberger
(74) *Attorney, Agent, or Firm*—Richard Aron Osman

(57) ABSTRACT

Methods for making siRNA comprise recombinantly coexpressing a Dicer protein with an R2D2 protein to form a complex comprising the R2D2 protein and the Dicer protein, and contacting the complex with a double-stranded (ds) RNA under conditions wherein the complex cleaves the dsRNA into siRNA. The R2D2 protein may be a *Drosophila* R2D2 protein and the Dicer protein may be a *Drosophila* Dicer-2 protein. The Dicer protein and the R2D2 protein may be coexpressed in insect cells, such as S2, Sf9 or Hi5 cells, using a baculovirus expression system.

2 Claims, No Drawings

R2D2: AN ENZYME OF RNA SILENCING

This work was supported by National Institute of Health Grant DC02539. The U.S. government may have rights in any patent issuing on this application.

INTRODUCTION

1. Field of the Invention

The field of this invention is an enzyme of RNA silencing.

2. Background of the Invention

RNA interference (RNAi) is a form of post-transcriptional gene silencing whereby dsRNA molecules trigger the sequence-specific degradation of cognate messenger RNA (mRNA) (1–3). The biological importance of RNAi is underscored by its wide conservation throughout metazoans and the existence of closely related systems in plants (co-suppression) and fungi (quelling) (4). Emerging evidence indicates that the RNAi and related pathways function in many fundamental biological processes including antiviral defense, development, and maintenance of genomic stability (4).

Experiments in the model *Drosophila* system indicate that the RNAi pathway consists of the initiation and effector steps. First, long dsRNA molecules are cleaved into 21 to 23-nucleotide (nt) small interfering RNA (siRNA) duplexes (5–8). Secondly, the siRNA is incorporated into a nuclease complex known as RNA-initiated silencing complex (RISC), and functions as a guide RNA to direct RISC-mediated sequence-specific mRNA degradation (6, 9–11). The endonuclease that processes dsRNA has been identified as Dicer, a family of large non-canonical RNaseIII enzymes (5). Two Dicer enzymes, DCR-1 and DCR-2, have been identified in *Drosophila* (5). It remains unclear how the siRNA generated by Dicer becomes incorporated into RISC. The two steps of the RNAi pathway appear to be closely coupled because the direction of dsRNA processing determines which strand of siRNA becomes the guiding strand for RISC (11).

Here we disclose the biochemical purification of siRNA-generating activity. The purified enzyme comprises two stoichiometric subunits, DCR-2 and a novel protein that we named R2D2 because it contains two dsRNA-binding domains (R2) and is associated with DCR-2 (D2). Tandem dsRNA-binding domains is a feature shared by the *C. elegans* RNAi protein RDE-4. Association with R2D2 does not affect the siRNA-generating activity of DCR-2. Rather, the DCR-2/R2D2 complex, but not DCR-2 alone, binds to siRNA and facilitates its incorporation into RISC. Our data reveal that R2D2 bridges the initiation and effector steps of the *Drosophila* RNAi pathway by facilitating the passage of siRNA from Dicer to RISC.

Relevant Literature

Recombinant Dicer proteins have been used to make siRNA; see, Myers et al., 2003, Nature Biotechnol 21, 324–8; Beach et al., 2003, U.S. Pat Appl Publ US 2003/0084471; Zhang et al., 2002, EMBO J 21, 5875–85; Dicer siRNA generation kit (Gene Therapy Systems, Inc., San Diego, Calif., Catalog No.T51001). Much of the sequence of the *Drosophila melanogaster* genome has been reported by Adams et al. 2000, Science 287, 2185–95, and an ORF with sequence identity to R2D2 is reported as NCBI locus CG7138 (Accession NM__135308). Aspects of this disclosure will be published by Liu et al., Sep. 26, 2003, Science vol.301, p. 1921–1925.

SUMMARY OF THE INVENTION

The invention provides methods and compositions for making siRNA. The general methods involve making siRNA by recombinantly coexpressing a Dicer protein with an R2D2 protein to form a complex comprising the R2D2 protein and the Dicer protein, and contacting the complex with a double-stranded (ds) RNA under conditions wherein the complex cleaves the dsRNA into siRNA. In particular embodiments, the R2D2 protein is a *Drosophila* R2D2 protein and the Dicer protein is a *Drosophila* Dicer-2 protein. The Dicer protein and the R2D2 protein may be coexpressed in insect cells, such as S2, Sf9 or Hi5 cells, using a baculovirus expression system.

The subject compositions include isolated and recombinantly expressed complexes of a Dicer protein and an R2D2 protein, cells and transgenic animals transformed with recombinant nucleic acid encoding an R2D2 protein or co-transformed with recombinant nucleic acid encoding a Dicer protein and an R2D2 protein, and kits for making siRNA, comprising an instructional medium describing or reciting a subject method copackaged with a reagent used in the method.

DESCRIPTION OF PARTICULAR EMBODIMENTS OF THE INVENTION

The inventors have isolated a novel protein, R2D2, and disclose how this protein may be used to stabilize coexpressed associated proteins, like Dicer proteins, and to modulate, particularly enhance Dicer protein expression, siRNA production, RISC loading, and RNA-initiated RNA silencing.

In one embodiment, the invention reconstitutes a step of RNA silencing by recombinantly coexpressing a Dicer protein with an R2D2 protein to form a complex comprising the R2D2 protein and the Dicer protein. As shown below, coexpression increases yield and stability of both proteins. The coexpressed proteins may be of any desired source material, and natural versions of both R2D2 and Dicer proteins are found in myriad species. For example, natural *Drosophila* R2D2 cDNA and expressed protein sequences are publically available as Flybase CG7138 and Genbank Accession NM__135308. Alternative species homologs are readily retrieved using conventional sequence algorithms and functionally confirmed using the functional assays below; e.g. Unigene retrieves the 12643664 human double-stranded RNA-binding protein Staufen homolog (Genbank Accession O95793). In a particular embodiment, the R2D2 protein is a *Drosophila* R2D2 protein and the Dicer protein is a *Drosophila* Dicer-2 protein. The proteins may be expressed in any convenient compatible protein expression system, including for example, in insect cells such as S2, Sf9 or Hi5 cells, using a baculovirus expression system. Alternative expression systems are well-known in the art.

Accordingly, the invention provides compositions comprising isolated or recombinantly expressed R2D2/Dicer complexes, and methods of making such complexes by assembling the R2D2 and Dicer component proteins, which may be made by coexpression. The R2D2/Dicer complex may also be assembled from separately expressed or purified components. For example, R2D2 may be isolated as an ~36 KDa protein that copurifies as siRNA generating activity with Dicer-2 (DCR-2) from a cytoplasmic (S100) extract of S2cells by sequential chromatographic steps as follows: S100 (100,000 g supernatant), ammonium sulfate precipitation, Phenyl-Sepharose (Amersham Biosciences), S-Sepharose (Amersham Biosciences), Q-Sepharose (Amersham Biosciences), hydroxyapatite and gel filtration, as described below.

The component proteins or complexes may be joined, covalently or noncovalently, with a wide variety of conjugates, including labels, tags, etc., particularly other polypeptide sequences. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

R2D2 proteins may be used to elicit an R2D2-specific antibody in a heterologous host (e.g a rodent or rabbit), etc, and provide R2D2-specific antigens and/or immunogens, especially when coupled to carrier proteins (see, e.g Harlow and Lane (1988) Antibodies, A Laboratory Manual, Cold Spring Harbor Laboratory). For example, polypeptides corresponding to R2D2-specific sequence are covalently coupled to keyhole limpet antigen (KLH) and the conjugate is emulsified in Freunds complete adjuvant. Laboratory rabbits are immunized according to conventional protocol and bled. The presence of R2D2-specific antibodies is assayed by solid phase immunosorbant assays, e.g. using immobilized R2D2. Such antibodies may be used, for example, for isolating siRNA generating enzyme complex from siRNA.

In a particular embodiment, the invention uses the Dicer/R2D2 complex to make siRNA, or enhance Dicer-made siRNA, by contacting the complex with a double-stranded (ds) RNA under conditions wherein the complex cleaves the dsRNA into siRNA. In particular embodiments, the dsRNA is a target dsRNA comprising a predetermined sequence. These methods may be used with any compatible dsRNA or dsRNAs, and may be practice in vitro, in isolated cells, or in vivo in animals, such as described below.

The invention also provides kits specifically tailored to practicing the subject methods, including kits comprising an instructional medium describing or reciting a subject method, with an associated, such as a copackaged reagent used in the method, such as a vector encoding the R2D2 protein, the dsRNA, etc. The recited reagent may be present in premeasured, prepackaged amounts.

Similarly, the invention also provides business methods specifically tailored to practicing the subject methods. For example, in one embodiment, the business methods comprise selling, contracting, or licensing a subject composition comprising an R2D2 protein, a subject kit, instructional medium, etc.

The subject compositions may also be used to modulate RNA interference. For example, R2D2 knockouts are silencing deficient. Similarly, point mutations in the dsRNA-binding domains of R2D2 abolish its ability to bind dsRNA, and provide dominant negative mutations for inhibiting RNA silencing. Analogously, transgenic cells and animals overexpressing R2D2 provide enhanced responses to long dsRNA-induced RNA interference. Such cells and animals may be used to assess gene function by RNAi. Methods for transforming cells and animals, particularly model animal systems such as Drosophila, C. elegans, zebrafish, mouse, rat, goat, etc., to make knockout, dominant negative and overexpressed versions of R2D2 are well-established in the art, and further described below.

The following experimental section and examples are offered by way of illustration and not by way of limitation.

EXAMPLES

Purification of the siRNA-generating Activity

We purified the siRNA-generating activity from the cytoplasmic (S100) extract of S2cells by a six-step chromatographic procedure. Briefly, approximately 500 ml of S100 (~8 mg/ml) prepared from 20 liters S2 cells were precipitated by ammonium sulfate at 25% saturation. After a 30-min 20,000 g spin, the supernatant was diluted 2.5 fold and loaded onto 5 ml Phenyl-Sepharose column. The activity was step eluted at ~4% (saturation) ammonium sulfate and, following overnight dialysis, was loaded onto a 1 ml Mono S HR 5/5 column. The peak activity was eluted at ~0.1 M NaCl by a 0–0.25 M gradient wash and loaded directly onto a 1 ml Mono Q HR 5/5 column. The peak activity was eluted at ~0.25 M NaCl by a 0.1–0.4 M gradient wash and, after a two-fold dilution, was loaded onto a 1 ml Hydroxyapatite column. The peak activity was eluted at 0.1% phosphate buffer (pH7.4) by a 0–0.15 gradient wash and, following a 4-hour dialysis, was concentrated on a 100 µl Mono S PC 1.6/5 column. Finally, the peak activity was fractionated by a 2.4 ml Superdex 200 PC 3.2/30 gel filtration column.

A single major peak of activity was observed at all steps and followed throughout purification. Two proteins, one at ~190 kDa and another ~36 kDa, showed perfect correlation with the enzymatic activity after the final gel filtration step. They were identified by mass spectrometry to be DCR-2 and a novel protein (Flybase CG7138; Genbank NM_135308), respectively. R2D2 bears 20.9% identity and 33.4% similarity to the C. elegans protein RDE-4, which also carries tandem dsRNA-binding domains and interacts with Dicer (16). Rde-4 was recently cloned as a gene mutated in a worm strain that is defective in the RNAi pathway (16, 17).

DCR-2/R2D2 is the Principal Dicer Enzyme in S2 Cells

Our purification results suggest that DCR-2 forms a stable complex with R2D2 and is the principal siRNA-generating enzyme in Drosophila S2 cells. To confirm this, we performed immunodepletion experiments using an antiserum directed against the carboxyl terminal 150 amino acids of R2D2. This R2D2 antibody depleted both R2D2 and DCR-2 proteins from S100. Consequently, the majority of siRNA-generating activities were removed from S100. On the contrary, the level of DCR-1, a previously proposed siRNA-generating enzyme (5), remained unchanged in the supernatant after R2D2 immunodepletion. This indicates that the majority of DCR-2, not DCR-1, is associated with R2D2 and is responsible for the siRNA-generating activity in S100. Furthermore, when S100was fractionated on a Q-Sepharose column, the peak of siRNA-generating activity correlated perfectly with DCR-2 and R2D2, but not DCR-1. Consistent with this, DCR-1 was not detected in the highly purified Dicer fractions by Western blotting.

To determine the contribution of DCR-1 and DCR-2 to siRNA production in Drosophila cells, we depleted either protein from S2 cells by soaking cells with the corresponding dsRNA. Interestingly, DCR-2 dsRNA treatment also caused a substantial reduction in the level of R2D2 protein. This was not simply due to cross targeting because the level of R2D2 mRNA was not affected. Likewise, R2D2 dsRNA treatment also reduced, although not as dramatically, the level of DCR-2. These results further confirm that DCR-2 and R2D2 form a stable complex and indicate that either protein alone is relatively unstable. While depletion of DCR-1 made no impact on siRNA production, knocking down DCR-2 resulted in a five-fold reduction in the siRNA-generating activity in whole cell lysate.

To clarify which of DCR-1 and DCR-2 is required for RNAi in S2 cells, we constructed an RNAi reporter cell line that contained a Luciferase and a LacZ reporter gene as well as a transgene expressing a 500-bp luciferase hairpin RNA. Thus, the expression of luciferase reporter was under constant suppression by the hairpin RNA via the RNAi pathway. However, introduction of dsRNA molecules targeting a specific component of the RNAi machinery would reduce its efficiency and thereby cause a temporary increase in luciferase production. We found that while DCR-1 dsRNA made no difference, DCR-2 or AGO-2 (a known RISC component) dsRNA resulted in an approximately two- or seven-fold increase in the relative luciferase/b-galactosidase activities, respectively. Taken together, these results demonstrate that the DCR-2/R2D2 complex, not DCR-1, is the principal siRNA-generating enzyme responsible for initiation of RNAi in *Drosophila* S2 cells.

R2D2 is Required for RNAi In Vivo

To determine if R2D2 is required for RNAi in vivo, we generated an r2d2 deletion mutant fly by P element mobilization. The r2d2 mutant flies were crossed with transgenic flies expressing green fluorescent protein (GFP) under the control of the ubiquitin promoter to generate homozygous r2d2; Ub-GFP mutant flies. We then collected 0-2 hour wild type or r2d2 mutant embryos for microinjection with GFP dsRNA. While introduction of GFP dsRNA effectively silenced the expression of green fluorescent proteins in wild type embryos, r2d2 mutant embryos were completely defective for the dsRNA-initiated RNAi response. Thus, we concluded that R2D2 is essential for the RNAi pathway in the fruitfly.

Reconstitution of the siRNA-Generating Activity by Recombinant Proteins

To reconstitute the siRNA-generating activity in vitro, we expressed polyhistidine (His)-tagged DCR-2 and R2D2 in insect cells using a baculovirus expression system and purified the recombinant proteins by Nickel affinity column followed by S- and Q-Sepharose chromatography. A mutant form of R2D2 was also generated with point mutations in the dsRNA-binding domains that abolish its ability to bind dsRNA. Our results showed that recombinant DCR-2 protein alone efficiently cleaved dsRNA into siRNA in an ATP- and dose-dependent manner. ATP could not be substituted by non-hydrolysable ATP-g-S, indicating that ATP hydrolysis is required for efficient siRNA production. This is consistent with previous studies conducted with crude *Drosophila* lysates (5, 8).

The recombinant DCR-2/R2D2 complex was also ATP-dependent and showed equivalent siRNA-generating activity as DCR-2. We performed kinetic studies using purified DCR-2 or DCR-2/R2D2 recombinant proteins and found no statistically significant difference in their Km or Kcat. Furthermore, the mutant DCR-2/R2D2$^M$ complex was as active in siRNA production as the wild type complex. These results indicate that association with R2D2 does not affect the ability of DCR-2 to recruit or cleave dsRNA. This finding is inconsistent with the proposed function of RDE-4 to recruit dsRNA to DCR-1 (the single Dicer enzyme in worms) for processing (16). However, R2D2 may stabilize DCR-2 and thereby positively regulate siRNA production in *Drosophila* cells. Consistent with this, we observed that DCR-2 and R2D2 were both expressed at much higher levels in insect cells when expressed jointly than separately.

The DCR-2/R2D2 Complex Binds siRNA

To track the fate of siRNA, we developed a gel shift assay to identify proteins that interact with siRNA. When radiolabeled 21-nt synthetic siRNA duplex was incubated with S2 cell lysate, a distinct mobility shift was observed on a native polyacrylamide gel. The formation of this siRNA/protein complex did not require ATP hydrolysis because it could be carried out at 4° C. and was not enhanced by addition of ATP. The binding of radiolabeled siRNA duplex could be competed out by excess cold double-stranded siRNA, but not by single-stranded siRNA or 23-bp double-stranded DNA oligonucleotides. Furthermore, when S100 was fractionated by Q-Sepharose column, the siRNA-binding activity correlated well with the siRNA-generating activity among different fractions. This indicated that DCR-2 and R2D2 were associated with the siRNA-binding activity. We then performed the gel shift assays in the presence of antibodies against DCR-2 or R2D2. Both antibodies resulted in a supershift that was absent when their preimmune sera were used instead. This indicated that DCR-2 and R2D2 were both present in this siRNA/protein complex.

When purified DCR-2, DCR-2/R2D2 and DCR-2/R2D2$^M$ recombinant proteins were examined for siRNA binding by the gel shift assay, wild type DCR-2/R2D2 complex, but not DCR-2 alone, bound to siRNA independent of ATP and produced a mobility shift indistinguishable from that in S100. The ability of the DCR-2/R2D2 complex to bind siRNA was greatly diminished by point mutations within the dsRNA-binding domains of R2D2. Thus, R2D2 is important for binding to the product (siRNA) rather than the substrate (dsRNA) of DCR-2. Furthermore, when DCR-2/R2D2 proteins and radiolabeled siRNA were exposed to ultraviolet (UV) light, both DCR-2 and R2D2 were crosslinked to the radiolabeled siRNA. This crosslinking was greatly diminished if the mutant DCR-2/R2D2$^M$ complex was used instead, although similar amounts of proteins were added as detected by Western blotting. We observed two R2D2-siRNA crosslinked bands, one at ~45 kDa and another ~52 kDa, apparently representing R2D2 proteins covalently linked to one or two siRNA strands since the estimated molecular weight of each 21-nt siRNA strand was ~7 kDa. This was confirmed by the downshift of both R2D2/siRNA crosslinked bands to the original position of ~38 kDa His$_6$—R2D2 protein following RNase treatment. These results indicate that DCR-2 and R2D2 bind to siRNA in a coordinate manner that is dependent upon the dsRNA-binding domains of R2D2.

R2D2 Facilitates siRNA Loading onto RISC

Based on the ability of the DCR-2/R2D2 complex to bind siRNA, we hypothesized that R2D2 might be involved in facilitating siRNA loading onto RISC. To test this hypothesis, we first separated the RISC activity from the Dicer activity in S100 by polyethylene glycol (PEG) precipitation, and then combined the partially purified RISC with recombinant Dicer proteins to reconstitute the RNAi reaction. Our data showed that while the majority of Dicer activity was precipitated by 10% PEG, a significant amount of RISC remained in the supernatant, which could be activated by addition of siRNA or dsRNA for sequence-specific mRNA degradation. The wild type DCR-2/R2D2 complex was much more effective than DCR-2 alone or the mutant complex in promoting the dsRNA-initiated RISC activity in the 10% PEG supernatant. At 3 nM concentrations, wild type DCR-2/R2D2 stimulated the RISC activity by more than seven-fold, whereas DCR-2 or DCR-2/R2D2$^M$ stimulated only by two-fold. Interestingly, the mutant complex blocked the RISC activity at 10 nM concentrations, indicating dominant-negative effects. Furthermore, similar phenomenon was observed in the siRNA-initiated RISC assay. Thus, the DCR-2/R2D2 complex could enhance the dsRNA- as well as the siRNA-initiated RISC activities. We further showed that this enhancement was not simply a result of siRNA stabilization by DCR-2/R2D2 by comparing the stability of radiolabeled siRNA in the RISC reactions described above.

To confirm that DCR-2/R2D2 enhanced RISC activities by facilitating incorporation of siRNA into RISC, we followed the association between AGO2, an essential component of RISC, and a 3'-biotinylated siRNA by precipitation using streptavidin beads. The biotinylated siRNA was as active as unmodified siRNA in inducing RISC activities in S100. However, streptavidin beads only brought down AGO2 protein when biotinylated siRNA was used, indicating that it was a specific interaction. We then performed RISC assays using biotinylated siRNA in 10% PEG supernatant alone or in combination with recombinant DCR-2, DCR-2/R2D2, and DCR-2/R2D2$^M$ proteins. Consistently, AGO2 proteins were only detected in the biotinylated siRNA precipitates when wild type DCR-2/R2D2 complex was used. Taken together, our results indicate that the DCR-2/R2D2 enzyme not only generates siRNA from dsRNA, but also binds to nascent siRNA and facilitates its loading onto RISC for sequence-specific mRNA degradation. The latter activity is dependent on the dsRNA-binding domains of R2D2.

REFERENCES

1. A. Fire et al., *Nature* 391, 806–11 (1998).
2. M. K. Montgomery, S. Xu, A. Fire, *Proc Natl Acad Sci USA* 95, 15502–7 (1998).
3. T. Tuschl, P. D. Zamore, R. Lehmann, D. P. Bartel, P. A. Sharp, *Genes Dev* 13, 3191–7 (1999).
4. G. J. Hannon, *Nature* 418, 244–51 (2002).
5. E. Bernstein, A. A. Caudy, S. M. Hammond, G. J. Hannon, *Nature* 409, 363–6 (2001).
6. P. D. Zamore, T. Tuschl, P. A. Sharp, D. P. Bartel, *Cell* 101, 25–33 (2000).
7. S. M. Elbashir, J. Martinez, A. Patkaniowska, W. Lendeckel, T. Tuschl, *Embo J* 20, 6877–88 (2001).
8. A. Nykanen, B. Haley, P. D. Zamore, *Cell* 107, 309–21 (2001).
9. S. M. Hammond, S. Boettcher, A. A. Caudy, R. Kobayashi, G. J. Hannon, *Science* 293, 1146–50 (2001).
10. S. M. Hammond, E. Bernstein, D. Beach, G. J. Hannon, *Nature* 404, 293–6 (2000).
11. S. M. Elbashir, W. Lendeckel, T. Tuschl, *Genes Dev* 15, 188–200 (2001).
12. P. Provost et al., *Embo J* 21, 5864–74 (2002).
13. H. Zhang, F. A. Kolb, V. Brondani, E. Billy, W. Filipowicz, *Embo J* 21, 5875–85 (2002).
14. R. F. Ketting et al., *Genes Dev* 15, 2654–9 (2001).
16. H. Tabara, E. Yigit, H. Siomi, C. C. Mello, *Cell* 109, 861–71 (2002).
17. A. Grishok, H. Tabara, C. C. Mello, *Science* 287, 2494–7 (2000).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of making siRNA in vitro, the method comprising the steps of:
    recombinantly coexpressing a *Drosophila* Dicer-2 protein with a *Drosophila* R2D2 protein to form a complex comprising the R2D2 protein and the Dicer-2 protein in vitro; and
    contacting the complex with a target double-stranded (ds) RNA comprising a predetermined sequence under cell-free, in vitro conditions wherein the complex cleaves the dsRNA into siRNA.

2. A method according to claim 1, wherein the Dicer-2 protein and the R2D2 protein are coexpressed using a baculovirus expression system in insect cells selected from the group consisting of S2, Sf9 and Hi5 cells.

* * * * *